(12) United States Patent
Holt

(10) Patent No.: US 7,773,460 B2
(45) Date of Patent: Aug. 10, 2010

(54) MEDICATION REGIMEN COMMUNICATOR APPARATUS AND METHOD

(76) Inventor: Lindsay Holt, 135 S. 300 West, Bountiful, UT (US) 84010

( * ) Notice: Subject to any disclaimer, the term of this patent is extended or adjusted under 35 U.S.C. 154(b) by 2041 days.

(21) Appl. No.: 10/287,256

(22) Filed: Nov. 4, 2002

(65) Prior Publication Data

US 2004/0088132 A1    May 6, 2004

(51) Int. Cl.
   G04B 47/00    (2006.01)
   G04B 45/00    (2006.01)
   G09D 3/00     (2006.01)
   G09F 9/00     (2006.01)

(52) U.S. Cl. .......................... 368/10; 368/41; 368/223; 40/107; 116/308; 283/2; 283/115

(58) Field of Classification Search ................ 368/280, 368/107, 10, 28, 41, 223; 283/81, 1, 2, 3, 283/4, 115, 900; 40/107, 110, 446; 116/298, 116/308
See application file for complete search history.

(56) References Cited

U.S. PATENT DOCUMENTS

| | | | | |
|---|---|---|---|---|
| 630,822 | A * | 8/1899 | Bates | 283/81 |
| 1,448,698 | A * | 3/1923 | Murdoch | 283/115 |
| 1,533,297 | A * | 4/1925 | Aller | 368/88 |
| 1,588,964 | A * | 6/1926 | Hutchins | 283/115 |
| 1,837,707 | A * | 12/1931 | Follows | 116/308 |
| 2,040,119 | A * | 5/1936 | Baxter | 116/308 |
| 3,921,568 | A * | 11/1975 | Fish | 116/308 |
| 3,964,196 | A * | 6/1976 | Ureta | 40/107 |
| 4,295,664 | A * | 10/1981 | Cutting | 283/115 |
| 4,490,711 | A | 12/1984 | Johnston | 340/309.4 |
| 4,523,852 | A | 6/1985 | Bauer | 356/421 |
| 4,614,360 | A * | 9/1986 | Sheehan et al. | 281/45 |
| 4,703,017 | A | 10/1987 | Campbell et al. | 436/501 |
| 4,786,596 | A | 11/1988 | Adams | 435/28 |
| 4,799,712 | A * | 1/1989 | Biava et al. | 462/67 |
| 4,815,767 | A * | 3/1989 | Lambert | 283/67 |
| 4,849,948 | A | 7/1989 | Davis et al. | 368/10 |
| 4,877,580 | A | 10/1989 | Aronowitz et al. | 422/58 |
| 5,031,937 | A * | 7/1991 | Nellhaus | 283/52.1 |
| 5,102,169 | A * | 4/1992 | Mayfield | 283/115 |
| 5,207,746 | A | 5/1993 | Jones | 283/81 |
| 5,261,702 | A * | 11/1993 | Mayfield | 283/115 |
| 5,271,172 | A * | 12/1993 | Ureta | 40/107 |
| 5,386,990 | A * | 2/1995 | Smith | 473/131 |
| 5,393,100 | A | 2/1995 | Coe | 283/115 |
| 5,431,450 | A | 7/1995 | Coleman | 283/62 |
| 5,591,645 | A | 1/1997 | Rosenstein | 436/514 |
| 5,646,913 | A * | 7/1997 | Quesenberry | 368/223 |

(Continued)

OTHER PUBLICATIONS www.dictionary.com definition of analog, Dec. 28, 2009.*

Primary Examiner—Vit W Miska
(74) Attorney, Agent, or Firm—Pate Pierce & Baird

(57) ABSTRACT

A "medication communicator" chart is used as a teaching tool to educate patients and to schedule events corresponding to a prescribed medication regimen. The "medication communicator" chart includes a scheduling graph having the shape of a 12-hour or 24-hour analog clock. The scheduling graph is divided into regions corresponding to each hour of a day for scheduling event information. Fields, on the "medication communicator" chart, are receptive to labels communicating information corresponding to numerous medications in the medication regimen. Timing indicators may be applied to the regions of the scheduling graph to indicate consumption or application times of each of the medications.

16 Claims, 12 Drawing Sheets

U.S. PATENT DOCUMENTS

| | | | |
|---|---|---|---|
| 5,758,096 A | 5/1998 | Barsky et al. | 395/203 |
| 5,954,641 A | 9/1999 | Kehr et al. | 600/300 |
| 5,958,536 A | 9/1999 | Gelsinger et al. | 428/40.1 |
| 5,995,938 A * | 11/1999 | Whaley | 705/3 |
| 6,018,289 A | 1/2000 | Sekura et al. | 340/309.4 |
| 6,085,752 A | 7/2000 | Kehr et al. | 128/897 |
| 6,102,855 A | 8/2000 | Kehr et al. | 600/300 |
| 6,130,100 A | 10/2000 | Jobling et al. | 436/518 |
| 6,169,707 B1 | 1/2001 | Newland | 368/10 |
| 6,303,081 B1 | 10/2001 | Mink et al. | 422/61 |
| 6,304,849 B1 | 10/2001 | Uecker et al. | 705/3 |
| 6,376,195 B1 | 4/2002 | Mapes | 435/7.1 |
| 6,574,165 B2 * | 6/2003 | Sharma et al. | 368/10 |
| 2001/0023548 A1 * | 9/2001 | Bundy | 40/446 |
| 2007/0287140 A1 * | 12/2007 | Liebowitz | 434/304 |

* cited by examiner

MEDICATION REGIMEN COMMUNICATOR APPARATUS AND METHOD

BACKGROUND

1. The Field of the Invention

This invention relates to medication regimens prescribed by caregivers and, more particularly, to novel systems and methods for communicating medication regimens to clients or patients.

2. The Background Art

As the field of medicine continues to advance, particularly with the emergence of many new and effective drugs, the average life span of human beings continues to increase. In many cases, a regimen prescribed to a client or patient by a caregiver may include numerous drugs or medications. Each medication may have a distinct dosage, timetable for consumption, method of consumption, along with distinct instructions and warnings corresponding thereto. In certain instances, the timing or dosage of a particular drug may change from day to day. Moreover, medications may be administered by a professional, a relative, or the patient. As the number of medications in a selected regimen increases, so does the complexity of the medication regimen and the likelihood of error by a caregiver or patient. The error may occur in communication of or in compliance with instructions provided by a healthcare professional.

During the training of medical professionals, considerable emphasis is placed on the importance of maintaining strict accuracy in the administration of medications. Errors or misuse of drugs and medications may be dangerous to a patient, undermine their efficacy, and be extremely costly. Since many patient's medication regimens are administered at home on an out-patient basis, they are effectively self-supervised. Methods are needed to simplify and manage the communication, administration, and tracking associated with consumption of medications, so that they may be properly administered. Moreover, the ability of patients to cope with the complexity of overseeing a medication regimen may be further complicated by the patient's illness. Other factors that may undermine a patient's ability to correctly follow a medication regimen may include caregivers's or a patient's age (youth or seniority), education, language barriers, mental condition, sight or hearing impairment, and aptitude.

Tools are needed by medical professionals and professional caregivers to properly communicate with and educate both patients and caregivers about medication regimens. Charts currently used to convey this information may be useful to the caregivers themselves and others who can become familiar with them over time. However, such charts may be confusing to patients due to age (youth or seniority), education, language barriers, mental condition, sight or hearing impairment, and aptitude. Moreover, charts suitable for use may prove insufficient as teaching tools to properly educate patients and amateur caregivers.

What is needed is a chart system and process that are simplified and structured in a manner that may allow use of clear visual, iconic communication enabling substantially all patients and caregivers of varied age and medical condition to successfully follow a medication regimen.

What is further needed is a charting system and method to overcome language barriers by providing terminology, color, and symbology that can be more universally understood.

What is further needed is a charting system and method to serve as a successful teaching tool for medical professionals and professional caregivers to properly educate clients, amateur caregivers, and patients of varied age and medical condition regarding a medication regimen.

What is further needed is a charting system and method that graphically illustrate to a client or patient proper times, medications, and dosages of a prescribed medication regimen.

Also needed is a system and method for tracking, by a patient, caregiver, or medical professional, the history of administration of medications. Doctors, nurses, and other need to know what has happened compared to what was prescribed. Patients need to know what was done. Anyone administering a medication may forget what has been done or whether it has been done as routines drag on and memories of events seem to blur together.

BRIEF SUMMARY AND OBJECTS OF THE INVENTION

In view of the foregoing, it is an object of the present invention to provide an apparatus and method for communicating a medication regimen, prescribed by a doctor or other caregiver, to a patient. A "medication communicator" chart, system, and method in accordance with the present invention may be used as a teaching tool to educate patients and to schedule events corresponding to a prescribed medication regimen. The "medication communicator" chart may include a scheduling graph having the shape of a 12-hour analog clock, 24-hour analog clock, or the like. This shape is used because it is universally understood and is more easily comprehended by the very young and elderly. In addition, the graphical nature of the analog clock may provide easier visualization over a typical rectangular chart or table. Moreover, poor eyesight is easily compensated by an analog dial, where written text may fail.

The scheduling graph may be divided into regions corresponding to each hour of a day. Fields, on the "medication communicator" chart may be receptive to labels communicating information corresponding to numerous medications in a prescribed medication regimen. Timing indicators may be applied to the regions of the scheduling graph to indicate consumption or application times of each of the medications.

Each of the medications may be readily distinguished from one another by assigning each medication a distinct color, pattern, symbol, texture, or the like. In addition, one embodiment "medication communicator" chart may include one or several fields receptive to labels printed with patient information, such as name, address, emergency contact information, identification number, if any, or any other desired patient information.

The "medication communicator" chart may include fields receptive to labels containing frequency information for consuming the medications. For example, in certain embodiments, an "every day" label may be applied to the chart to indicate that a patient is to take a medication every day. Likewise, "every other day" labels or labels designating specific days of the week may be applied to the chart to indicate when a medication is to be taken.

A label sheet may provide labels to be adhered to the "medication communicator" chart in accordance with the invention. The labels may include a pair of medication labels for each medication in the regimen. One label may be adhered to the "medication communicator" chart. The other corresponding label may be adhered directly to the packaging of the referenced medication. Each label may have the same color, pattern, symbol, texture, or the like, so that a selected medication may be referenced directly to the chart.

Each medication may include corresponding timing indicator labels characterized by the same color, pattern, symbol, texture, or the like, as the medication label. These timing indicator labels may be adhered to the regions of the scheduling graph to indicate the time a selected medication is to be taken. In certain embodiments, the "medication communicator" chart may include calendars printed thereon to assist a patient in keeping track of the medication regimen.

In certain embodiments, the scheduling graph may be represented by two separate 12-hour analog clocks to represent the A.M and P.M, hours, respectively. This embodiment may help further clarify what medications are to be taken in the A.M. hours as opposed to the P.M. hours by applying the corresponding timing indicators to separate scheduling graphs. In this embodiment, timing indicator labels having an A.M. or P.M. designation may be eliminated. In selected embodiments, the A.M. and P.M. scheduling graphs may be identified by an A.M. and P.M. icon, respectively.

In certain embodiments in accordance with the invention, a system for record keeping may be used. For example, when a medication of a medication regimen is ingested or applied, a record-keeping label, pin, magnet, magnetic label, marker, or the like, may be used on a calendar to record consumption times of medications in the medication regimen. Thus, a patient may keep records of the regimen and provide feedback to a caregiver that a medication regimen has been executed correctly.

BRIEF DESCRIPTION OF THE DRAWINGS

The foregoing and other objects and features of the present invention will become more fully apparent from the following description, taken in conjunction with the accompanying drawings. Understanding that these drawings depict only typical embodiments of the invention and are, therefore, not to be considered limiting of its scope, the invention will be described with additional specificity and detail through use of the accompanying drawings in which.

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 10, is not intended to limit the scope of the invention, but is merely representative of certain presently preferred embodiments of the system in accordance with the invention.

The term "patient" as used throughout the specification and claims, means any person or even an animal requiring management of a medication regimen. The terms "medicine" and "medication" as used throughout the specification and claims mean prescription and nonprescription drugs, vitamins, supplements, herbs, foods, bandages or other wraps, first aid devices, cleaning solutions, and the like. The term "caregiver" as used throughout the specification and claims means any doctor, physician, nurse, medical practitioner, family member, individual, patient, or and the like responsible for adherence to a medication regimen.

The embodiments of systems, methods, and devices in accordance with the invention will be best understood by reference to the drawings, wherein like parts are designated by like numerals throughout.

Figure 1:
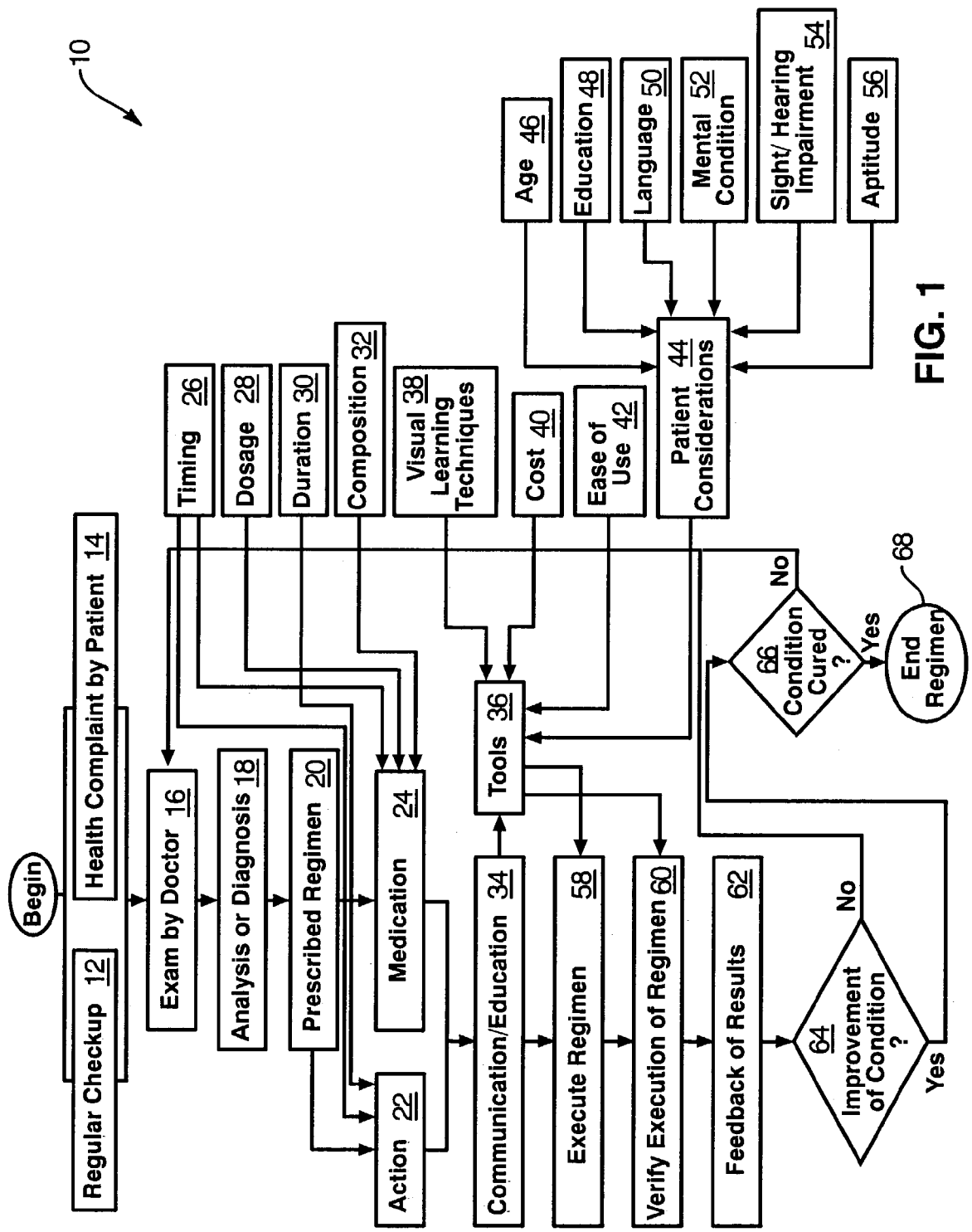
FIG. 1 is a flow chart illustrating a generalized treatment process.

Referring to FIG. 1, a treatment process 10 may typically be initiated by either a regular checkup 12 of a patient or by a health complaint 14 initiated by a patient. As a result, an examination 16 of the patient may be performed by a doctor or caregiver. The examination 16 may result in an analysis 18 or a diagnosis 18 by a health professional. Depending on the result of the analysis or diagnosis 18, a doctor may prescribe a particular regimen 20 to the patient. For some over-the-counter medications, any caregiver may establish a regimen. However, a medical professional is more likely to do so. This regimen 20 may include either actions 22, medication 24, or a combination thereof 22, 24.

If medication 24 is prescribed, the prescription may include timing information 26 for ingesting or applying the prescribed medication, a required dosage 28 of the prescribed medication, a duration 30 for taking the prescribed medication, and information on the actual composition 32 being prescribed.

Once a medication 24 or action regimen 22 is prescribed, a caregiver may need to communicate 34 or educate 34 this regimen 20 to the patient or to a nonprofessional caregiver. The communication 34 or education process 34 may be facilitated by the use of selected tools 36. These tools 36 may assist a patient or client in executing 58 a regimen, or may help a caregiver in actually verifying 60 that the medical regimen has been executed correctly. Tools 36 may include various visual learning tools and techniques 38.

Other factors that may be important in implementing effective tools 36 to communicate or educate 34 a patient may include cost 40, ease of use 42 of the tool 36, as well as other patient considerations 44. By patient considerations 44 is meant taking into account factors that may determine if a tool 36 in successful at communicating or educating a patient. These may include a patient's age 46, education 48, language 50, mental condition 52, sight or hearing impairment 54, aptitude 56, or the like. An effective tool 36 may be effective in overcoming any or all of these communication barriers 46, 48, 50, 52, 54, 56.

Once a regimen has been successfully communicated 34, a patient or client may need to actually follow 58 or execute 58 the regimen without supervision or with nonprofessional supervision. Thus where a patient is mentioned herein, a typically nonprofessional caregiver (or possibly other caregiver) may execute appropriate actions. Once the regimen has been executed 58, a caregiver may need to verify 60 that the regimen has been properly executed. This may require providing feedback 62 or results 62 to a caregiver.

After receiving feedback 62 that a regimen 20 has been properly executed, if the patient's condition has not improved at a test 62, the caregiver may choose to perform another examination 16 and prescribe another regimen 20. If the patient's condition has improved according to the test 62, but the patient's condition remains uncured, then the caregiver may again choose to perform another examination 16 and prescribe another regimen 20. However, if the condition has improved at test 62 and the condition has been successfully treated and cured in the patient, then the prescribed regimen may be ended 68.

Figure 2:
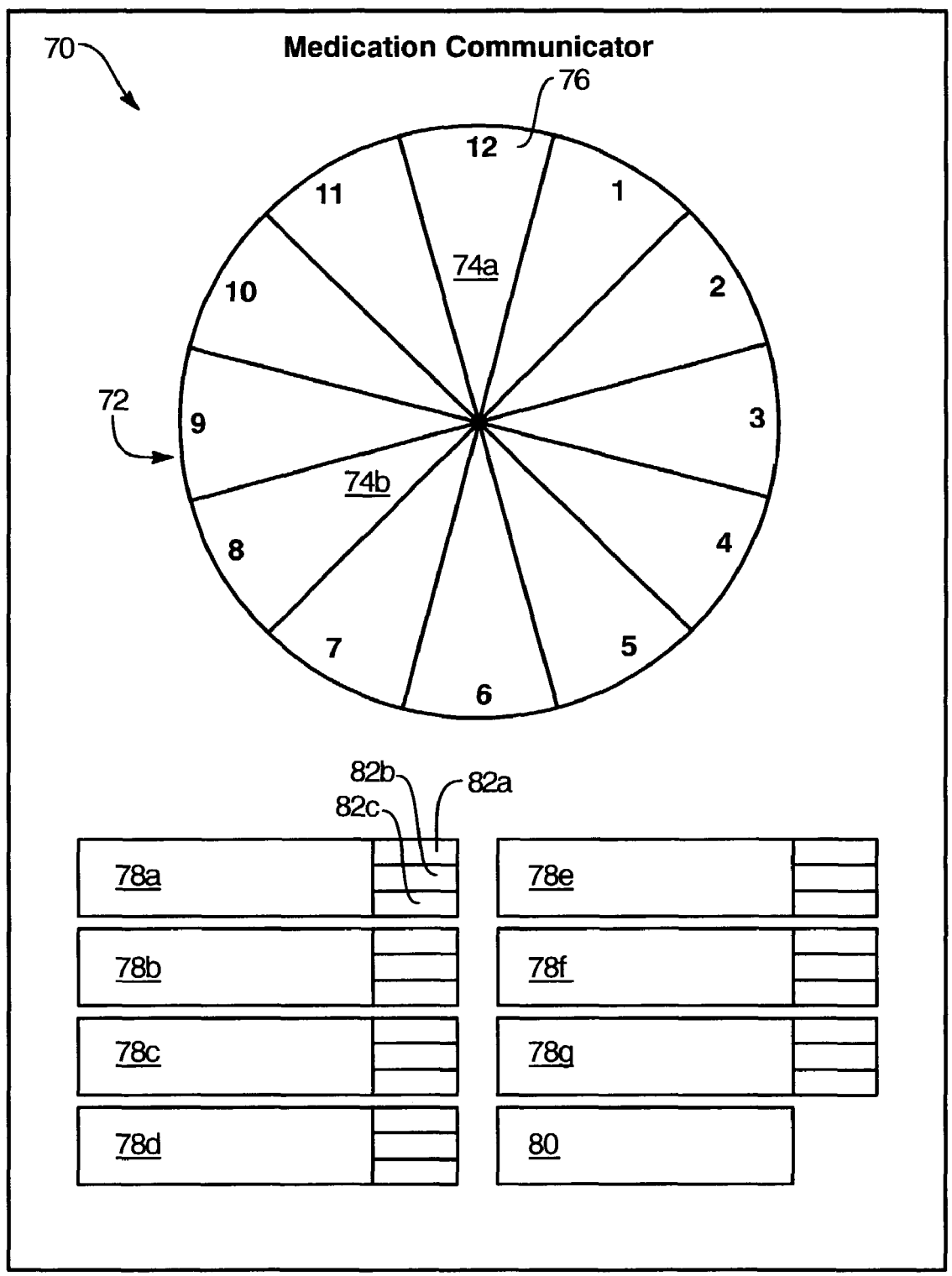
FIG. 2 is a schematic block diagram of on embodiment of a "medication communicator" chart in accordance with the present invention.

Referring to FIG. 2, a "medication communicator" chart 70 may include a scheduling graph 72 to display scheduling information related to the medication regimen 24 of a patient or client. In certain embodiments, the scheduling graph 72 may be presented in the form of a twelve-hour analog clock. The twelve-hour analog clock may be used because it is universally understood and because it has become a worldwide standard. This may prove particularly important in communicating regimen 20 information to a young or elderly patient, or if a language barrier is present.

The scheduling graph 72 may be divided into regions 74 to produce a plurality of scheduling fields 74 so that different medications of a medication regimen 24 may be scheduled. Each scheduling field 74 may correspond to a time 76 indicating when the selected medication is to be ingested or applied by the patient. As illustrated, the scheduling graph 72 is represented by a twelve-hour analog clock. However, in other selected embodiments, a twenty-four hour analog clock may also be used. The "medication communicator" chart 70 may be printed on a variety of substrates including, but not limited to, paper, cardboard, laminate materials, glass, metal, plastics, and the like.

The "medication communicator" chart 70 may further include a plurality of medication fields 78, each corresponding to a distinct medication in a medication regimen 24. Each of the medication fields 78 may include notes and administration comments pertaining to a particular medication. For example, notes may include the strength of the medication and directions from the caregiver related to using the particular medication.

The "medication communicator" chart 70 may further include a patient information field 80 which may include desired patient information such as the patient's name, identification number if needed, address, emergency contact information, as well as other desired information. Each of the medication fields 78 may include corresponding fields 82 where timing information may be located. These spaces 82 may contain labels which indicate the timing or frequency with which a particular medication should be used. For example, a field 82a may, for example, contain or include a label that informs the patient that a medication should be taken every day, every other day, or on selected days of the week. In addition, the "medication communicator" chart 70 may include a plurality of fields 78 to list each of the medications of a medication regimen 24.

Because of the clock-like layout of certain embodiments of the "medication communicator" chart 70, the chart 70 may be more easily understood by patients of all ages 46, particularly the young and elderly, or of disparate educations 48, languages 50, mental conditions 52, or aptitudes 56. Because of the graphical layout 72 of the "medication communicator" chart 70, medication regimen information may be more easily communicated by a caregiver to a patient or client. Moreover, because of the clock-like layout of the "medication communicator" chart 70, a patient or client may be able to easily understand the times a particular medication is to be taken by simply referencing the chart with the time on a normal twelve-hour analog clock.

The "medication communicator" chart 70 may be used to schedule medications of a prescribed medication regimen 24. However, one of ordinary skill in the art will be able to recognize that the chart 70 may be used to schedule not only medication 24, but also actions 22, or compliance with other instructions. In addition, the chart 70 may be used outside of the medical industry for many types of event scheduling. The color, pattern, symbol, or texture coding may be used in numerous applications to provide a simple, easy-to-follow, universally understood, scheduling system.

Figure 3:
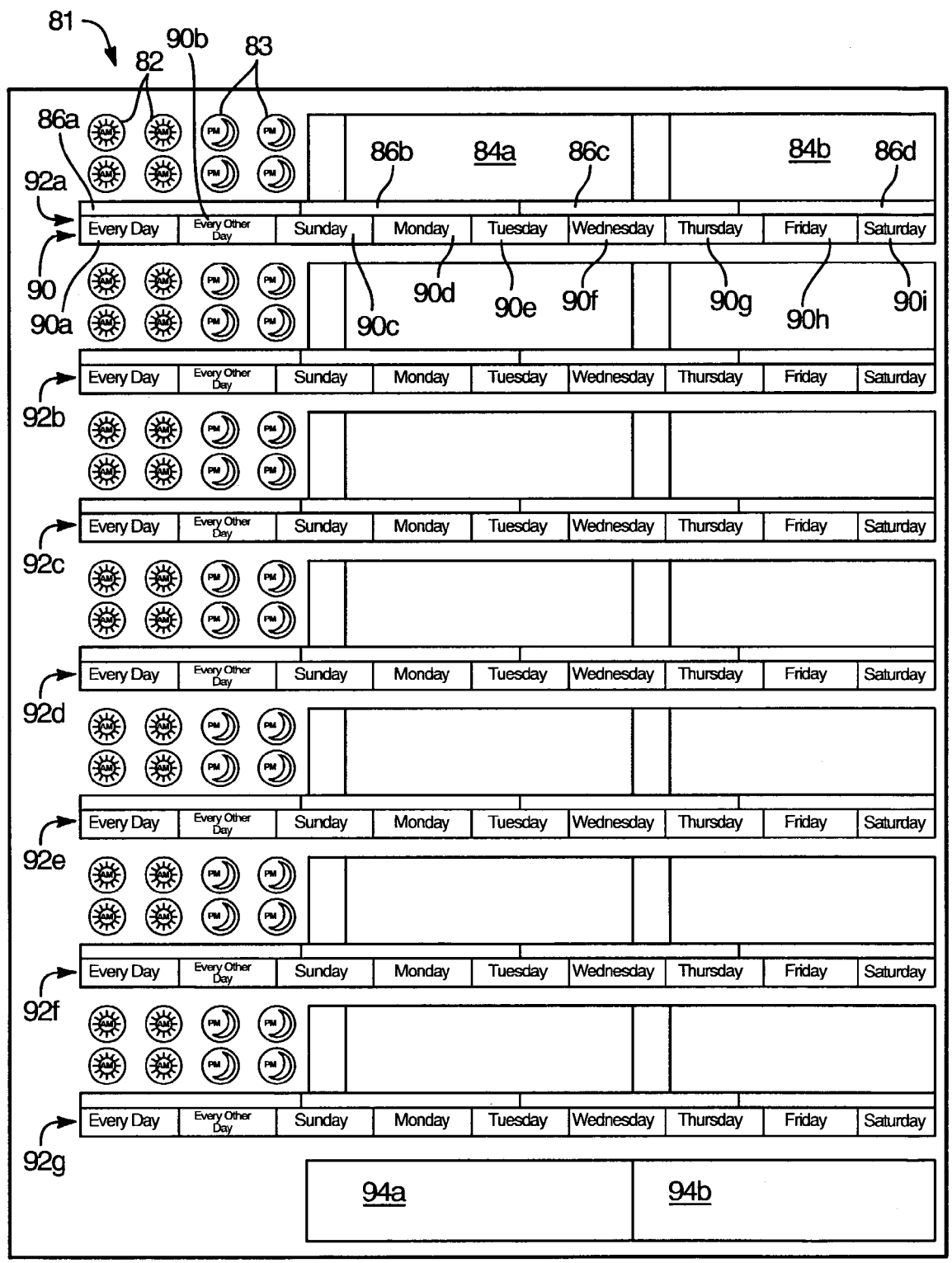
FIG. 3 is a schematic block diagram of one embodiment of a label sheet in accordance with the present invention.

Referring to FIG. 3, a label sheet 81 may include a plurality of labels 81 which may be applied to a "medication communicator" chart 70. For example, A.M. timing indicator labels 82 may be applied to the scheduling graph 72 to indicate when medications are to be taken by a patient or client in the "A.M." hours. Likewise, P.M. timing indicator labels 83 may also be applied to a scheduling graph 72 to indicate when medications are to be taken in the "P.M." hours. For example, if a medication is to be taken by a patient at 8:00 o'clock A.M., a label 82 may be applied to the space 74b. However, if a medication is to be taken at 8:00 o'clock P.M. in the evening, a label 83 may be applied to the scheduling field 74b. Likewise, the other labels 82, 83 may be applied to the various fields 74 of the scheduling graph 72 to indicate other times when medications are to be taken or applied by a patient.

The label sheet 81 may also include a plurality of medication labels 84a, 84b to provide information related to a particular medication. One medication label 84a may be applied to the "medication communicator" chart 70 in the medication field 78a. A second medication label 84b may be applied directly to the packaging or enclosure of a particular medication. In addition, if syringes or other implements are used to dispense or apply a particular medication, measurement labels 88 may be used to indicate the measure, amount, etc. of medication to be dispensed. In addition, timing indicator labels 90 may be provided in order to indicate to a patient the timing or frequency with which to take a particular medication.

For example, if a medication is to be taken every day, an "every day" label 90a may be used. However, if a particular medication is to be taken every other day, an "every other day" 90b label may be used. Likewise, if a medication is to be taken on some other day of the week, then labels 90c, 90d, 90e, 90f, 90g, 90h, 90i may be used to indicate the other days of the week. Thus a label set 92a may be used to provide information to client regarding a particular medication. The label set 92a may be identified by a particular color, symbol or pattern to identify a particular medication. In other embodiments, a particular texture may be used to help blind or sight-impaired patients to identify a particular medication. In the case that a patient is color-blind, a particular pattern or cross-hatching may be used to help the patient identify a particular medication.

In a similar manner, other label sets 92b, 92c, 92d, 92e, 92f, 92g may be assigned a different color, pattern, symbol, texture, or the like to identify other medications in a medication regimen 24. The medication information labels 84 may be configured to attach to a wide variety of medication containers including, but not limited to, bottles, tubes, inhalers, packages, boxes, blister packs, syringes, and the like.

In addition, medication information may be printed on the labels 84 using common typewriters or software templates. A particular software template may be configured so that data may be entered directly into fields 84, 94 of the label sheet 81 by a personal computer. In other embodiments, special software may be programmed so that data may be entered and then formatted to print on the labels 84, 94.

The label sheet 81 may also include one or a plurality of patient information labels 94a, 94b. These information labels 94a, 94b may include information corresponding to a particular patient such as name, identification number, address, emergency contact information, and the like. The labels 94a, 94b may then be removed from the label sheet 81 and applied to the "medication communicator" chart 70 in the field 80.

Figure 4:
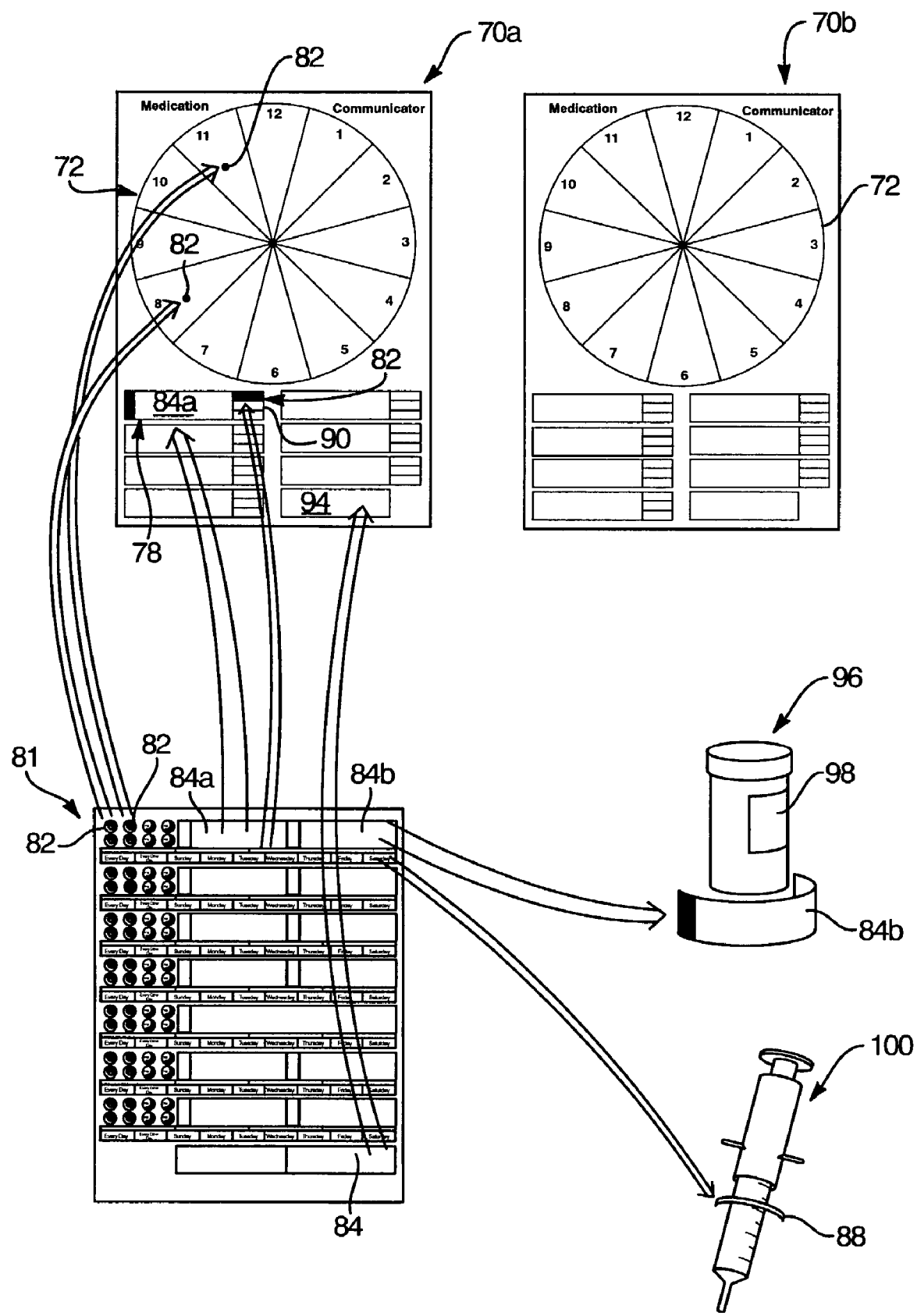
FIG. 4 is a flow diagram of one embodiment of a method of using the present invention.

Referring to FIG. 4, a caregiver may use a pair of "medication communicator" charts 70a, 70b. A first "medication communicator" chart 70a may be prepared for the caregiver's records. A second "medication communicator" chart 70b may be prepared to assist the patient or client. Labels may be removed from the label sheet 81 and applied to the "medication communicator" chart 70 according to a medication regimen. For example, a timing indicator label 82 may be removed from the label sheet 81 and applied to the "medication communicator" chart 70a to indicate that a particular medication is to be taken at 12:00 o'clock A.M.

Likewise, in another example, a timing indicator label 82 may be removed from the label sheet 81 and applied to the "medication communicator" chart 70a to indicate that a medication is to be taken or applied at 8:00 o'clock A.M. Likewise, if a medication is to be taken in the evening, one of the labels 83 may be applied to the "medication communicator" chart 70a in order to indicate what time in the evening the medication is to be taken.

In a similar manner, a medication label 84a may be removed from the label sheet 81 and applied to the "medication communicator" chart 70a to provide information pertaining to a first medication in a medication regimen 24. A second medication label 84 may be removed from the label sheet 81 and may be applied to a particular medication 96, such as a bottle 96 of prescription drugs. The prescription medication 96 may already include an information label 98 containing information pertaining to the medication. The medication label 84 may be adhered to the medication 96 such that the label does not hide or cover up information contained on the label 98.

In certain embodiments, the label 84 may be clear in order not to hide the inscription on the label 98. If a syringe 100, cup, spoon, or other implement 100 is to be used to dispense a particular medication, a measurement label 88 may be removed from the label sheet 81 and applied to the implement 100 or syringe 100 to indicate to the patient a particular measurement or grade to fill the syringe 100 or implement 100. In a like manner, a patient information label 94 may be imprinted with desired patient or client information and may be removed from the label sheet 81 and applied to the "medication communicator" chart 70a.

Figure 5:
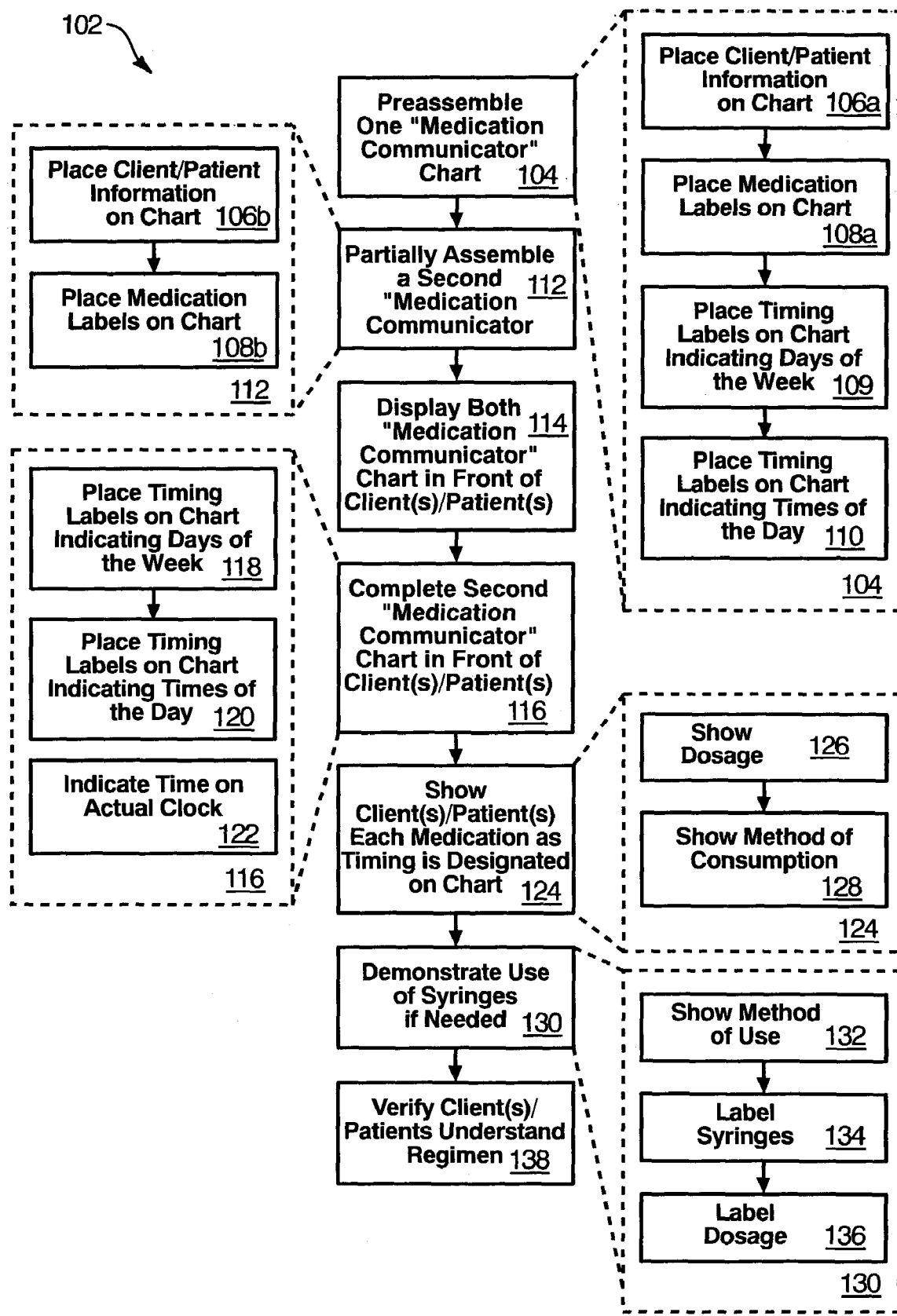
FIG. 5 is a flow diagram illustrating one embodiment of an education process in accordance with the present invention.

Referring to FIG. 5, while continuing to refer generally to FIGS. 1 through 4, an education process 102 may include preassembling 104 a first "medication communicator" chart. A preassembly process 104 may include first applying 106a a client or patient information label 94 to the chart 70, applying 108a medication labels 84a to the chart 70, applying 109 timing labels 90 to the chart indicating the days of the week, and applying 110 timing labels 82, 83 to the chart 70 indicating particular times of day.

A second step 112 may include partially assembling 112 a second. "medication communicator" chart 70. The chart 70 may be partially assembled 112 by first applying 106b client or patient information 94 to the chart 70 and then applying 108b medication labels 84 to the chart 70. A caregiver may then take the first preassembled "medication communicator" chart and the second partially assembled chart and display 114 both "medication communicator" charts 70 in front of a particular client or patient.

The assembly of the second "medication communicator" chart 70 may then be completed 116 while the client or patient observes. This may include first applying 118 timing labels 90 to the chart 70 indicating the days of the week, applying 120 timing labels 82, 83 to the chart indicating the times of day each medication is to be taken, and then indicating 122 the time on an actual clock in order to help the patient be visually reminded to remember when to take the medication. Thus, the client or patient may observe the assembly of the second "medication communicator" chart 70 by the caregiver. This may assist the learning process and provide a visual aid that may be more easily remembered.

As a caregiver is completing the second chart 70, the caregiver may show 124 the client or patient each medication as the timing is designated on the chart 70. This may include showing 126 the dosage to the client, as well as showing 128 the method of preparation, application, or consumption of the medication. If an implement (e.g. syringe) 100 is needed to dispense a particular medication, the measurement may be shown on the grading of the implement 100 at this time using the labels 88. This may include showing 132 a patient how to use the implement 100, labeling 134 the implement 100 with the correct medication information, and using the labels 88 to indicate 136 the correct dosage of medication. Once the medication regimen 24 is properly demonstrated to the client or patient, the caregiver may then use various methods to verify that the patient understood the regimen 24.

Figure 6:
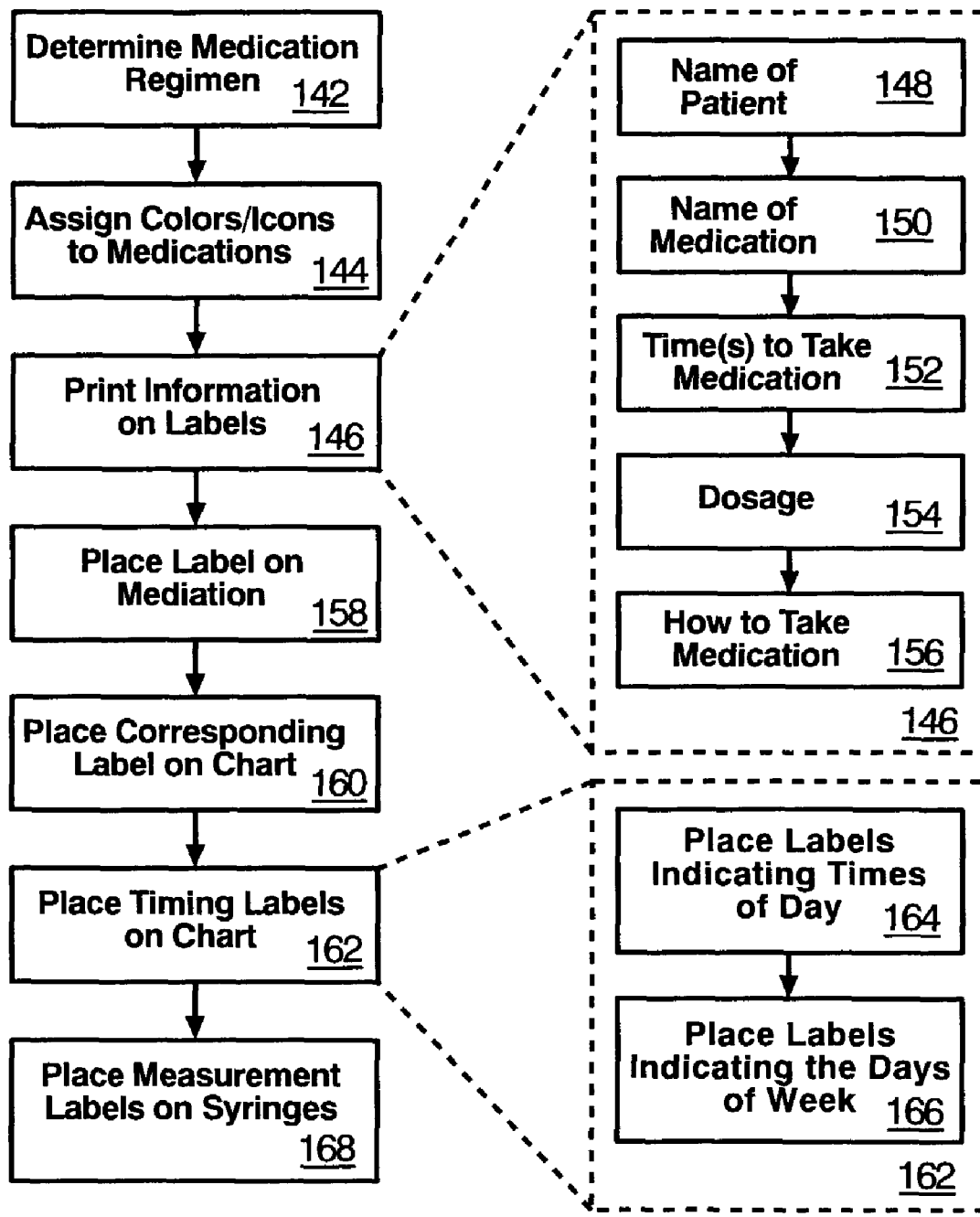
FIG. 6 is a flow diagram illustrating one embodiment of an assembly process in accordance with the present invention.

Referring to FIG. 6, an assembly process 140 of a "medication communicator" chart 70 may include initially determining 140 a medication regimen 24. Colors, symbols, patterns, textures, or other identifiers may be assigned 144 to each medication in the medication regimen 24. Any and all writing and coloring may be done in braille. After an identifier is assigned 144, medication information may be printed on the labels of the label sheet 81. This may include information such as the name 148 of the patient, the name 150 of the medication or composition, times 152 to take the medication, the dosage 154 of the medication to be ingested or applied, directions 156 on taking the medication, and the like.

Once the proper information is printed on the labels 84, the information labels 84 may then be applied 158 to each of the medications in the medication regimen 24. Corresponding labels 84 may then be applied 160 to the "medication communicator" chart 70. Once the information labels 84 are applied 160 to the "medication communicator" chart 70, the timing labels 82, 83 may then be applied 162 to the chart 70. This may include applying 164 the labels 82, 83 such that they indicate 164 the times of day, and applying the labels 90 indicating 166 the particular days of the week that the medication is to be taken. Once the timing labels 82, 83, 90 are applied 162 to the chart 70, measurement labels 88 may be applied 168 to any syringes 100, if used.

Figure 7:
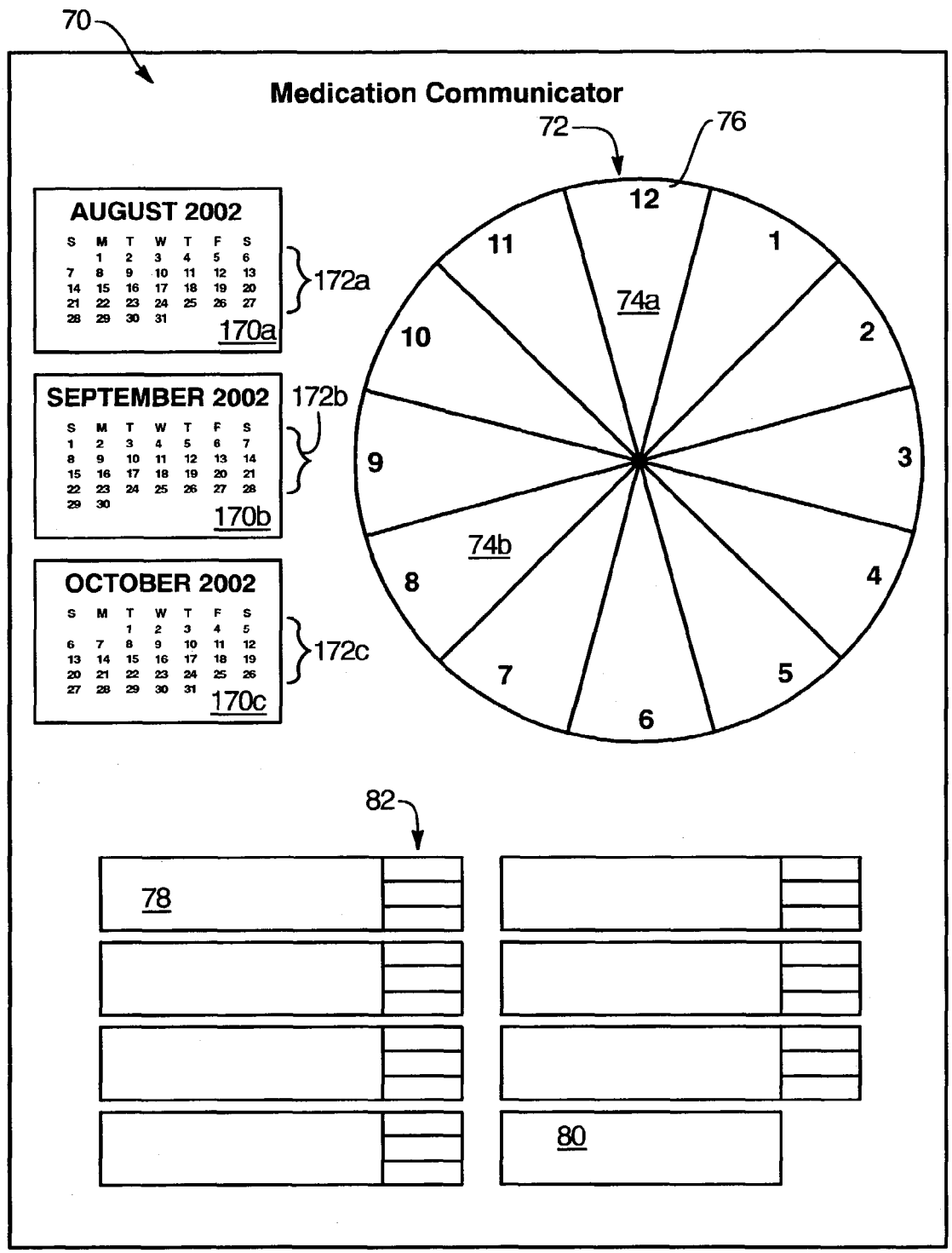
FIG. 7 is a schematic block diagram of an alternative embodiment of the "medication communicator" chart in accordance with the invention.

Referring to FIG. 7, in an alternative embodiment, the "medication communicator" chart 70 may include one or a plurality of calendars 170a, 170b, 170c indicating even and odd days 172a, 172b, 172c of the week. The even and odd days 172a, 172b, 172c may be used to schedule when particular medications are to be taken.

Figure 8:
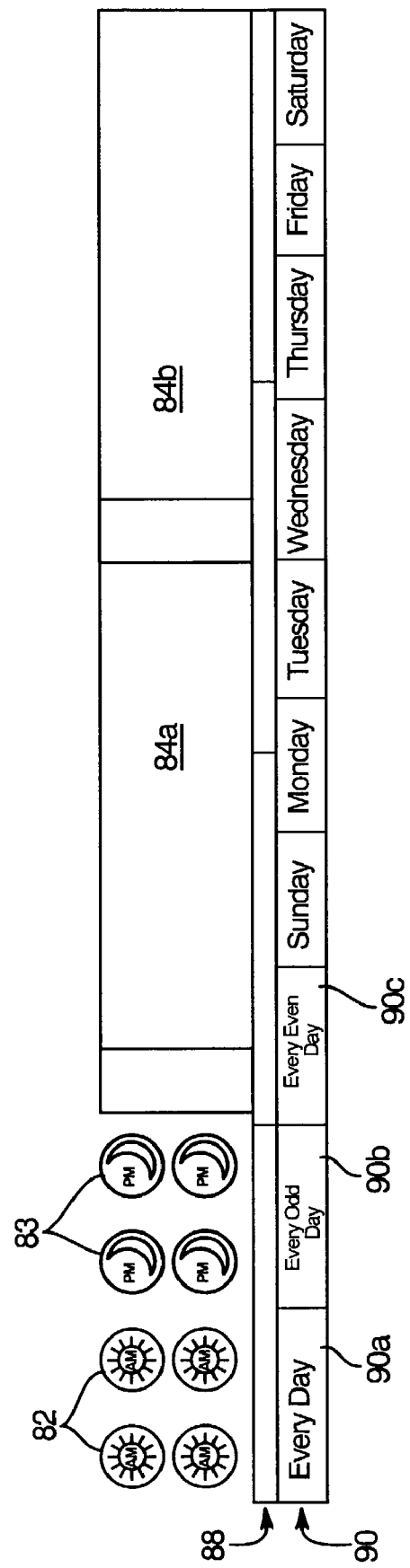
FIG. 8 is a schematic block diagram of labels that may be used in accordance with the "medication communicator" chart of FIG. 7.

For example, referring to FIG. 8, labels 92 assigned to a particular medication, may include an "every day" label 90a, an "every odd day" label 90b, and an "every even day" label 90c. This method may assist in eliminating confusion caused by the "every other day" label 90b described in FIG. 3. For example, under certain circumstances, a patient may forget to keep track of what days correspond to "every other day." With respect to the "every odd day" label 90b, a patient or client may simply refer to the calendars 170a, 170b, 170c, and take a selected medication on the odd days of the months 170a, 170b, 170c. Likewise, with respect to the "every even day" label 90c, a patient or client may simply refer to the calendars 170a, 170b, 170c and take a selected medication on the even days of the months 170a, 170b, 170c. Alternatively, the specific administration days of a week may be named, such as, for example, Monday and Thursday of each week.

Figure 9:
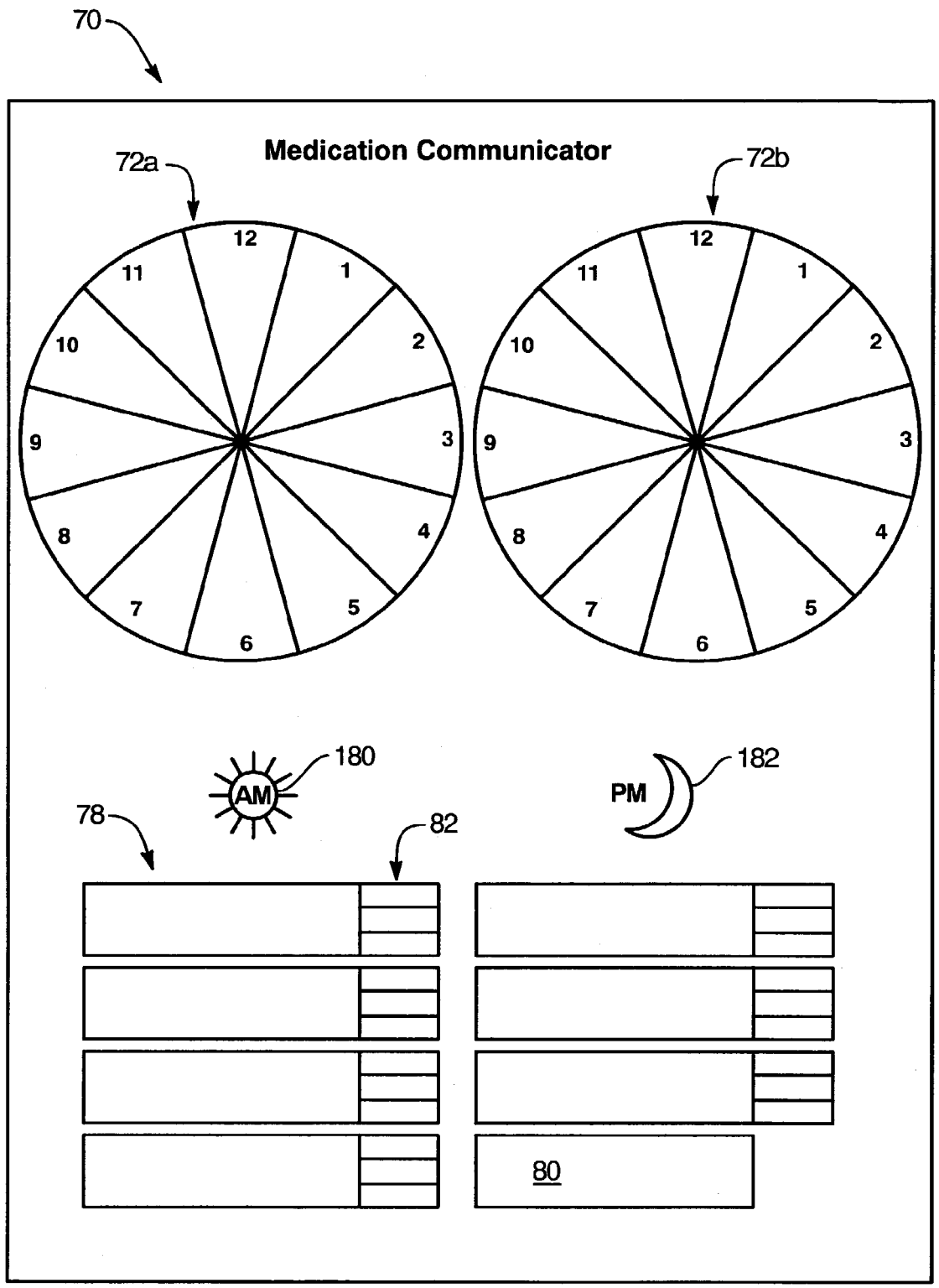
FIG. 9 is a schematic block diagram of another alternative embodiment of the "medication communicator" chart in accordance with the invention.

Referring to FIG. 9, in selected embodiments, the "medication communicator" chart 70 may include two scheduling graphs 72a, 72b. A first scheduling graph 72a may be used to establish an A.M. medication schedule and second scheduling graph 72b may be used to establish a P.M. medication schedule. This may help eliminate confusion caused by using one scheduling graph 72 to represent both A.M. and P.M. hours. The two scheduling graphs 72a, 72b may continue to represent a standard twelve-hour clock face, but may be effective to schedule events over a twenty-four hour day.

In certain embodiments, an A.M. icon 180 may be used to identify a first scheduling graph 72a and a P.M. icon 182 may be used to identify a second scheduling graph 72b. The icons 180, 182 may be located anywhere on the "medication communicator" chart 70 as long as they may be correctly identified with the corresponding scheduling graphs 72a, 72b. In selected embodiments, the icons 180, 182, may be located outside or inside the scheduling graphs 72a, 72b.

Figure 10:
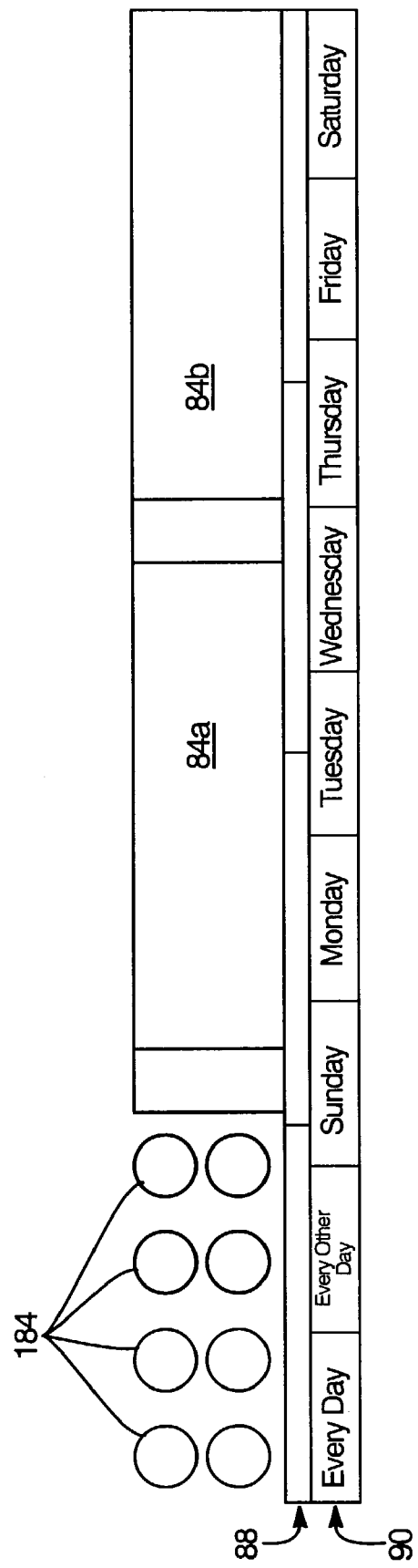
FIG. 10 is a schematic block diagram of labels that may be used with the "medication communicator" chart illustrated in FIG. 9.

Accordingly, referring to FIG. 10, the timing indicator labels 82, 83 illustrated in FIGS. 3 and 8 may simply be represented by labels 184 lacking any A.M. or P.M. designation. These labels 184 may then be applied to either of the A.M. or P.M. scheduling graphs 72a, 72b illustrated in FIG. 9 to schedule a selected event. By using two scheduling graphs 72a, 72b, any identifiers designating the labels 184 as either A.M. or P.M. labels 82, 83 are unnecessary.

Figure 11:
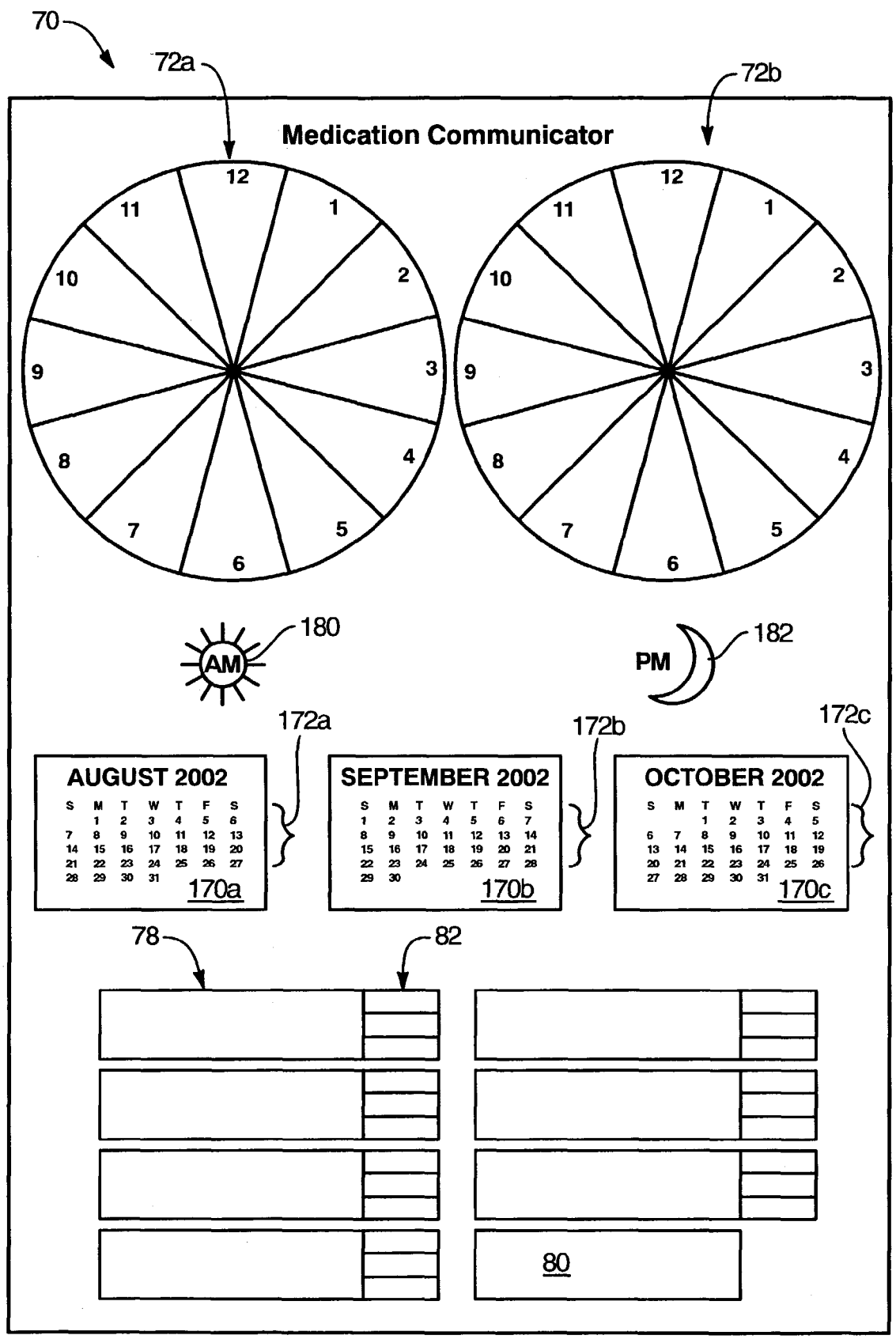
FIG. 11 is a schematic block diagram of another alternative embodiment of the "medication communicator" chart in accordance with the invention.

Referring to FIG. 11, the "medication communicator" chart 70 may include both a pair of scheduling graphs 72a, 72b, as well as calendars 170a, 170b, 170c, to identify the days 172a, 172b, 172c of the month. This chart 70 may provide the advantages of the chart 70 illustrated in FIG. 7 as well as the chart 70 illustrated in FIG. 9. A client or patient may easily identify events over a complete twenty-four day, eliminating the need for A.M. and P.M. timing labels 82, 83. In addition, the calendars 170a, 170b, 170c, may aid the patient or client in identifying odd, even, or specified days of the week to take a selected medication. As was previously described with respect to FIG. 9, A.M. and P.M. icons 180, 182 may be used to identify each scheduling graph 72a, 72b.

Figure 12:
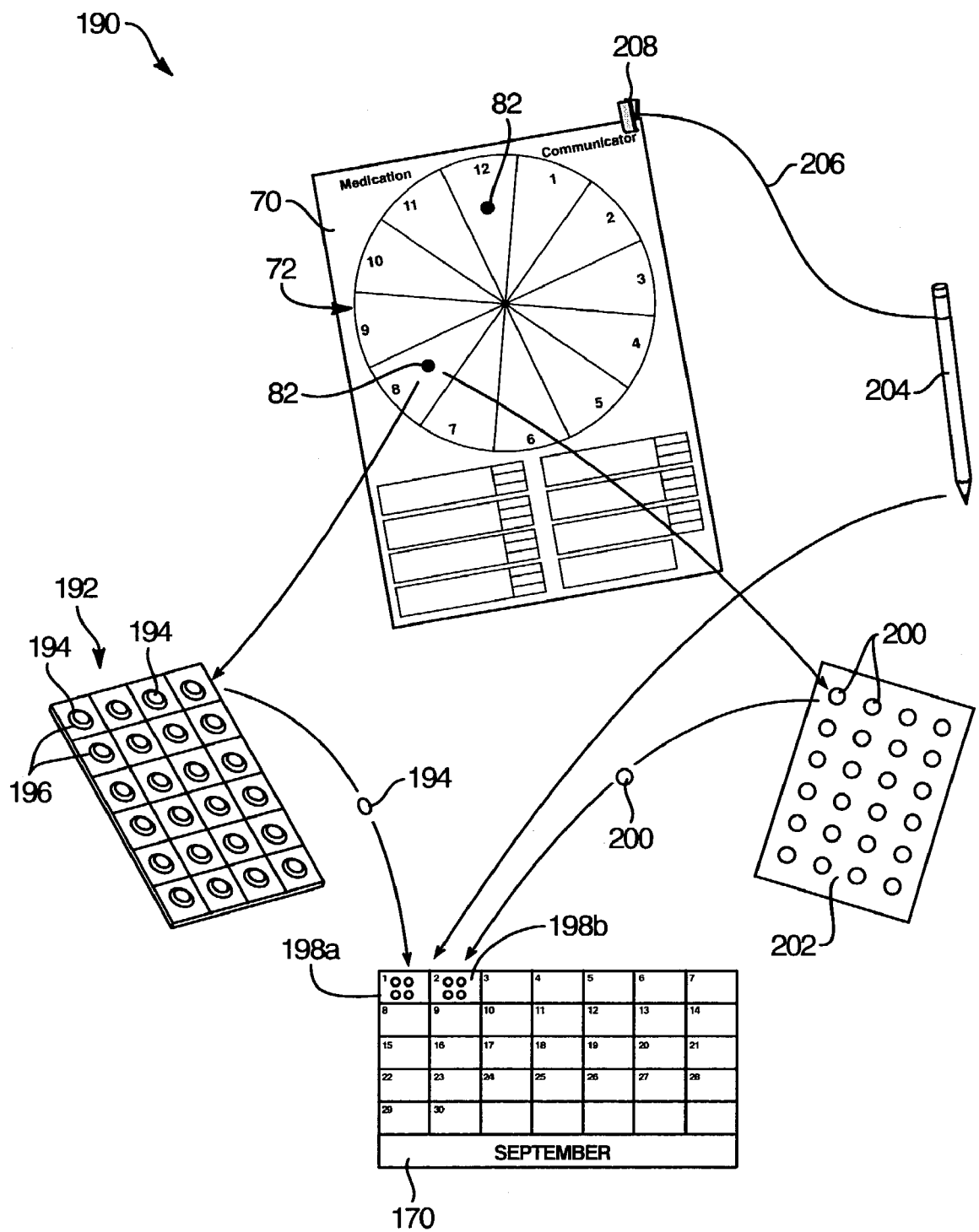
FIG. 12 is a flow chart illustrating a method for maintaining records in a medication regimen in accordance with the present invention.

With respect to FIG. 12, a method for maintaining records 190 of the execution of a medical regimen 24 may be used in accordance with the present invention. For example, in certain embodiments, a timing label 82 may be used to identify a time for taking a selected medication. A medication 196 may be contained in a blister pack 192 or other suitable packaging 192. In one selected embodiment, labels 194 may be used to cover each pill or tablet 196 in the blister pack 192. When a pill or tablet 196 is removed from the blister pack 192, the label 194 may be first removed from the blister pack. This label 194 may then be applied to a calendar 170 in a field indicating a particular day 198a. As each successive pill or tablet 196 is removed from the blister pack 192, the labels 194 may be applied to the calendar 170. Thus, a method of record keeping 190 may be provided to keep track of a client's or patient's actual administration of a medication regimen 24.

In another embodiment, a record label sheet 202 may be used to track a client's or patient's medication regimen 24. For example, when a medication is taken corresponding to an event indicated by a timing label 82, a sticker or label 220 may be removed from the label sheet 202 and applied to the calendar 170. Each time a medication is ingested or applied, another label or sticker 200 may be applied to a particular day 198 of the calendar 170. In certain embodiments, reusable indicators 200, such as magnetic labels or reusable tacks or pins, may be used to indicate when a mediation has been taken on the calendar 170. Likewise, the calendar 170 may be constructed from a variety of materials including paper, cardboard, wood, laminates, plastics, a bulletin board material, or some other like material. In another embodiment, the labels 200 may include a particular texture such as braille which might be used by a blind or sight-impaired patient.

In another embodiment, a record marker 204 may be used to keep track of events on the "medication communicator" chart 70. When a medication is taken, the record marker may be used to annotate the event on the calendar 170. In certain embodiments, the record marker may be a dry-erase marker 204 and the calendar 170 may be a dry-erase white board. The marker 204 may also include a tether 206 to tie the marker to the "medication communicator" chart 70, or the calendar 170.

The present invention may be embodied in other specific forms without departing from its essential characteristics. The described embodiments are to be considered in all respects only as illustrative, and not restrictive. All changes that come within the meaning and range of equivalency of the description are to be embraced within their scope.

What is claimed and desired to be secured by United States Letters Patent is:

1. A method for communicating a medical regimen to a patient, the method comprising:
   providing a scheduling device comprising
      a scheduling graph fixed to a supporting substrate,
      a reference chart positioned on the substrate in close proximity to the scheduling graph,
      the scheduling graph having a shape corresponding to a clock face representing at least one of a 12-hour, circular, analog clock and a 24-hour, circular, analog clock,
      the scheduling graph, further comprising markings spaced to divide an area thereof into regions corresponding to hours of a day,
      the scheduling graph further being fixed to be non-rotating with respect to a support underlying the scheduling graph,
      the reference chart further comprising a plurality of fields sized and shaped to receive therein labels affixed thereto,
      the reference chart, wherein each field of the plurality of fields further comprises an information region and at least one frequency region corresponding thereto, the information region and frequency region being distinguished from one another by at least one of size and shape,
   providing a sheet comprising a plurality of sets of labels, each set thereof comprising
      members, each being a label selectively removable from the sheet and comprising a material adherent to at least one of the scheduling graph and the reference chart, a visual feature unique to the each set and shared by the members of the set, the members, further comprising an information label having a surface prepared to receive an identification of a medication, and shaped to match the shape of the information region of a field of the reference chart, the members, further comprising a plurality of frequency labels, each specifying at least one day, being shaped to match the shape of the frequency region of a field of the reference chart and distinct from the shape of the information label, the members, further comprising a plurality of timing labels, each timing label being distinguished from both the information label and each of the frequency labels by at least one of size and shape; and providing instructions to a caregiver of the patient, effective to prepare the sheet, imprinted with information, reflecting the medical regimen, on at least one of the sets of labels.

2. The method of claim 1, wherein the providing instructions further comprises providing software effective to imprint the sheet.

3. The method of claim 2, wherein the providing instructions further comprises providing software comprising a template and executable to receive data entered by the caregiver for imprinting on labels of the sheet.

4. The method of claim 1, wherein the providing instructions further comprises providing software comprising a template and executable to receive data entered by the caregiver for imprinting on labels of the sheet.

5. A method for communicating a medical regimen to a patient, the method comprising:

obtaining a scheduling device comprising a scheduling graph fixed to a supporting substrate, a reference chart positioned on the substrate in close proximity to the scheduling graph, the scheduling graph having a shape corresponding to a clock face representing at least one of a 12-hour, circular, analog clock and a 24-hour, circular, analog clock, the scheduling graph, further comprising markings spaced to divide an area thereof into regions corresponding to hours of a day, the scheduling graph further being fixed to be non-rotating with respect to a support underlying the scheduling graph, the reference chart further comprising a plurality of fields sized and shaped to receive therein labels affixed thereto, the reference chart, wherein each field of the plurality of fields further comprises an information region and at least one frequency region corresponding thereto, the information region and frequency region being distinguished from one another by at least one of size and shape, obtaining a sheet comprising a plurality of sets of labels, each set thereof comprising members, each being a label selectively removable from the sheet and comprising a material adherent to at least one of the scheduling graph and the reference chart, a visual feature unique to the each set and shared by the members of the set, the members, further comprising an information label having a surface prepared to receive an identification of a medication, and shaped to match the shape of the information region of a field of the reference chart, the members, further comprising a plurality of frequency labels, each specifying at least one day, being shaped to match the shape of the frequency region of a field of the reference chart and distinct from the shape of the information label, the members, further comprising a plurality of timing labels, each timing label being distinguished from both the information label and each of the frequency labels by at least one of size and shape; and preparing the sheet, imprinted with information, reflecting the medical regimen, on at least one of the sets of labels.

6. The method of claim 5, wherein the preparing further comprises obtaining software effective to imprint the sheet in accordance with instructions from a caregiver to the patient.

7. The method of claim 6, wherein the preparing further comprises running, on a computer, the software and imprinting labels of the sheet.

8. The method of claim 7, wherein the software further comprises a template and is executable to prompt the caregiver and receive data entered by the caregiver in accordance with the template.

9. The method of claim 5, wherein the preparing further comprises running, on a computer, the software and imprinting labels of the sheet.

10. The method of claim 9, wherein the software further comprises a template and is executable to prompt the caregiver and receive data entered by the caregiver in accordance with the template.

11. The method of claim 4, further comprising:

imprinting an information label of a first set of the plurality of sets with information identifying a medication; and removing from the sheet from the first set the information label;

placing the information label on the information region of a first field of the plurality of fields on the reference chart.

12. The method of claim 11, further comprising:

removing from the sheet, from the first set, a first frequency label; and adhering the first frequency label on a frequency region of the first field.

13. The method of claim 12, further comprising:

removing from the sheet, from the first set, a first timing label; and adhering the first timing label on a region of the scheduling graph.

14. The method of claim 5, wherein the visual feature is a property selected from the group consisting of a color, a pattern, a symbol, a word, and a texture.

15. An apparatus for communicating a medical regimen to a patient, the apparatus comprising:

a scheduling device comprising a scheduling graph fixed to a supporting substrate, a reference chart positioned on the substrate in close proximity to the scheduling graph, the scheduling graph having a shape corresponding to a clock face representing at least one of a 12-hour, circular, analog clock and a 24-hour, circular, analog clock, the scheduling graph, further comprising markings spaced to divide an area thereof into regions corresponding to hours of a day, the scheduling graph further being fixed to be non-rotating with respect to a support underlying the scheduling graph, the reference chart further comprising a plurality of fields sized and shaped to receive therein labels affixed thereto, the reference chart, wherein each field of the plurality of fields further comprises an information region and at least one frequency region corresponding thereto, the information region and frequency region being distinguished from one another by at least one of size and shape; and a sheet comprising a plurality of sets of labels, each set thereof comprising members, each being a label selectively removable from the sheet and comprising a material adherent to at least one of the scheduling graph and the reference chart, a visual feature unique to the each set and shared by the members of the set, the members, further comprising an information label having a surface prepared to receive an identification of a medication, and shaped to match the shape of the information region of a field of the reference chart, the members, further comprising a plurality of frequency labels, each specifying at least one day, being shaped to match the shape of the frequency region of a field of the reference chart and distinct from the shape of the information label, the members, further comprising a plurality of timing labels, each timing label being distinguished from both the information label and each of the frequency labels by at least one of size and shape.

16. The apparatus of claim 15, further comprising instructions directed to a caregiver of the patient, effective to prepare the sheet, imprinted with information, reflecting the medical regimen, on at least one of the sets of labels.

* * * * *